United States Patent
Fayaz et al.

(10) Patent No.: US 8,571,299 B2
(45) Date of Patent: Oct. 29, 2013

(54) IDENTIFYING DEFECTS

(75) Inventors: Mohammed F. Fayaz, Pleasantville, NY (US); Julie L. Lee, Wappingers Falls, NY (US); Leah M. Pastel, Essex, VT (US); Maroun Kassab, Quebec (CA)

(73) Assignee: International Business Machines Corporation, Armonk, NY (US)

( * ) Notice: Subject to any disclaimer, the term of this patent is extended or adjusted under 35 U.S.C. 154(b) by 548 days.

(21) Appl. No.: 12/871,039

(22) Filed: Aug. 30, 2010

(65) Prior Publication Data

US 2012/0050728 A1    Mar. 1, 2012

(51) Int. Cl.
*G06K 9/00* (2006.01)

(52) U.S. Cl.
USPC .......................................... 382/145

(58) Field of Classification Search
USPC ......... 382/141–149, 218, 209, 216, 254, 293, 382/296; 348/92
See application file for complete search history.

(56) References Cited

U.S. PATENT DOCUMENTS

| | | | |
|---|---|---|---|
| 6,338,001 B1 | 1/2002 | Steffan et al. | |
| 6,563,324 B1 | 5/2003 | Nichani | |
| 6,778,695 B1 | 8/2004 | Schellenberg et al. | |
| 6,792,366 B2 * | 9/2004 | Hosoya et al. | 702/83 |
| 6,882,745 B2 | 4/2005 | Brankner et al. | |
| 6,886,153 B1 | 4/2005 | Bevis | |
| 6,952,653 B2 * | 10/2005 | Toth et al. | 702/35 |
| 6,966,047 B1 | 11/2005 | Glasser | |
| 7,072,786 B2 | 7/2006 | Coldren et al. | |
| 7,135,344 B2 | 11/2006 | Nehmadi et al. | |
| 7,343,583 B2 | 3/2008 | Keck et al. | |
| 7,368,713 B2 | 5/2008 | Matsui | |
| 7,570,796 B2 | 8/2009 | Zafar et al. | |
| 7,760,929 B2 * | 7/2010 | Orbon et al. | 382/148 |
| 7,844,934 B2 * | 11/2010 | Ono et al. | 716/106 |
| 2003/0022401 A1 | 1/2003 | Hamamatsu et al. | |
| 2003/0223639 A1 | 12/2003 | Shlain et al. | |
| 2006/0269120 A1 | 11/2006 | Nehmadi et al. | |
| 2006/0291714 A1 | 12/2006 | Wu et al. | |
| 2007/0052963 A1 | 3/2007 | Orbon et al. | |
| 2009/0034831 A1 | 2/2009 | Amanullah et al. | |

OTHER PUBLICATIONS

Yang, Hyunjo, et al., "Systematic Defect Filtering and Data Analysis Methodology for Design Based Metrology", Research & Development Division, Mar. 23, 2009, pp. 1-8.

* cited by examiner

*Primary Examiner* — Daniel Mariam
(74) *Attorney, Agent, or Firm* — Cantor Colburn LLP; Ian MacKinnon

(57) ABSTRACT

Identifying systematic defects in wafer processing including performing defect inspection of a plurality of wafers, identifying defects in each of the plurality of wafers as not being associated with a trivial and/or known root cause, determining a physical location on each wafer where each of the defects occurs and correlating the physical locations where each of the defects occurs with cell instances defined for those physical locations.

18 Claims, 9 Drawing Sheets

IDENTIFYING DEFECTS

BACKGROUND

Aspects of the present invention are directed to identifying defects in pluralities of wafers by correlating defects to design structure.

In wafer manufacturing processes, in-line inspection tools are used to detect and to report wafer visual defects by comparing wafer images at chip-to-chip locations. Defects are found by inspections performed on each manufactured layer where the wafer images do not match. Reported defects are stored in computer data storage for further analysis. This process is normally referred to interactive defect analysis.

Typically, the number of defects for a specific wafer may count in the hundreds of thousands in early technology development stages. Therefore, interactive defect analysis is prohibitive and automated data analysis is often required. Generally, this type of automated data analysis is aimed at multiple objectives. These include assisting in tuning manufacturing processes to minimize the number of defects, determining physical layout structures that are prone to defects so that learned structures can be incorporated into the design for manufacturing methodologies so that chips become easier to manufacture, determining non-killer defects and providing feedback for tuning the inspection process to minimize oversensitivity and to prevent artifacts from being reported as defects and keeping the analysis algorithm as simple as possible to thereby provide a methodology that is practical from a computational perspective.

With this in mind, existing tools focus mainly on visualizing the defects, and providing basic statistics like defect densities. Some attempt to compare layout shapes of the inspected layer around the defects. This type of analysis is known as pattern matching and has many drawbacks. For example, pattern matching is computationally expensive and forces developers to employ tools using empirical methods (e.g., comparing shape densities or some other easy to calculate properties). Also, orientation independence is hard to solve and is also computationally expensive, high defect coordinate accuracy is required and defects are often caused by interactions between layout structures at multiple layers, such as the inspected layer and the layers below it.

SUMMARY

In accordance with an aspect of the invention, a method of identifying systematic defects in wafer processing is provided and includes performing defect inspection of a plurality of wafers, identifying defects in each of the plurality of wafers as not being associated with a trivial and/or known root cause, determining a physical location on each wafer where each of the defects occurs and correlating the physical locations where each of the defects occurs with cell instances defined for those physical locations.

In accordance with another aspect of the invention, a method for identifying systematic defects in wafer processing is provided and includes inputting defect data for a plurality of wafers into a processing unit of a computing device having a non-transitory computer readable medium on which executable instructions are stored, which, when executed, cause the processing unit to analyze wafer level defect data to identify defects with trivial and/or known root causes, ascertain defect coordinates, translate defects coordinates to reticle and design coordinate spaces, and extract placement information for each cell instance of each design and map the defects to the reticle and design coordinate spaces.

In accordance with another aspect of the invention, a method for identifying systematic defects in wafer processing is provided and includes wafer based defect analysis, wafer-to-reticle defect stacking, reticle-to-design defect mapping and design-to-cells defect mapping.

In accordance with yet another aspect of the invention, a system to identify systematic defects in wafer processing is provided and includes a wafer inspection apparatus to inspect a plurality of wafers for defects and to generate defect data in accordance with results of the inspection, a networking unit coupled to the wafer inspection apparatus and a computing device, coupled to the networking unit, to receive the defect data generated by the wafer inspection apparatus by way of the networking unit, the computing device including a processing unit and a non-transitory computer readable medium on which executable instructions are stored, which, when executed, cause the processing unit to identify defects in each of the plurality of wafers as not being associated with trivial and/or known root causes, to determine a physical location on each wafer where each of the defects occurs and to correlate the physical locations where each of the defects occurs with cell instances defined for those physical locations.

BRIEF DESCRIPTIONS OF THE SEVERAL VIEWS OF THE DRAWINGS

The subject matter regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

DETAILED DESCRIPTION

In accordance with aspects of the present invention, defects not associated with trivial and/or known root causes are identified and correlated with design structures based on a transformation of defect coordinates to design coordinate space and then to cell coordinate spaces. Defects are then clustered using simple proximity techniques into hard repeaters and clouds of defects. The clustering is performed at the chip level and at each cell. This technique exploits the hierarchical nature of physical designs where a layout structure is reused hundreds or thousands of times on the chip, often with various orientations and mirroring possibilities, such as in very large scale integration (VLSI) designs that use 8 orthogonal possibilities of orientation and mirror.

Figure 1:
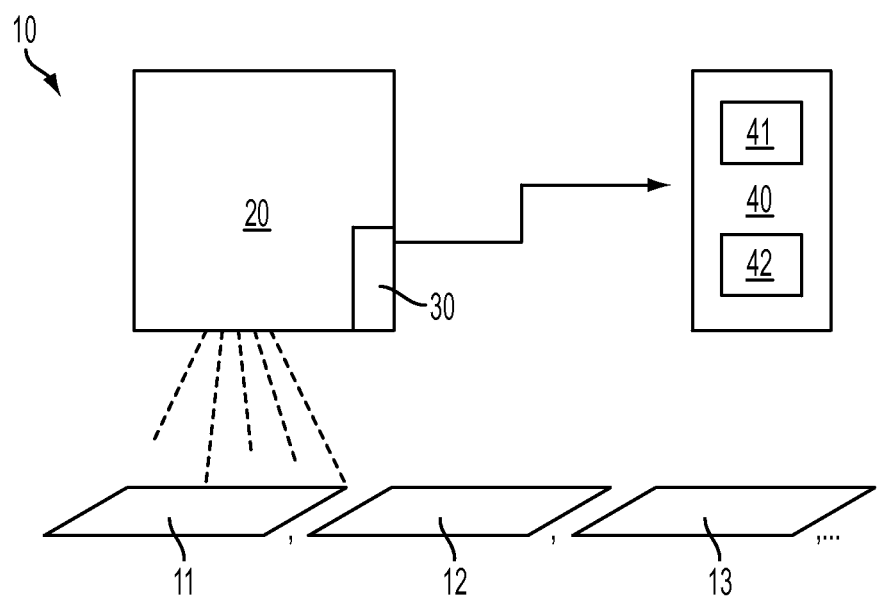
FIG. 1 is a schematic diagram of a system for identifying systematic defects in wafer processing.

With reference to FIG. 1, a system 10 is provided to identify systematic defects in wafer processing for pluralities of wafers 11, 12, 13, . . . . The system 10 includes a wafer inspection apparatus 20, such as an optical device that is well known in the field, to inspect the plurality of the wafers for defects and to generate defect data in accordance with results of the inspection. The system 10 further includes a networking unit 30 coupled to and disposed in signal communication with the wafer inspection apparatus 20 and a computing device 40.

The computing device 40 includes a processing unit 41 and a non-transitory computer readable medium 42. The computing device 40 is coupled to and disposed in signal communication with the networking unit 30 to thereby receive the defect data generated by the wafer inspection apparatus 20. The non-transitory computer readable medium 42 has executable instructions stored thereon, which, when executed, cause the processing unit 41 to identify in each of the plurality of wafers the defects that are not associated with known root causes and then to correlate their locations with cell instances defined for those physical locations. These operations will be described further below.

Figure 2A:
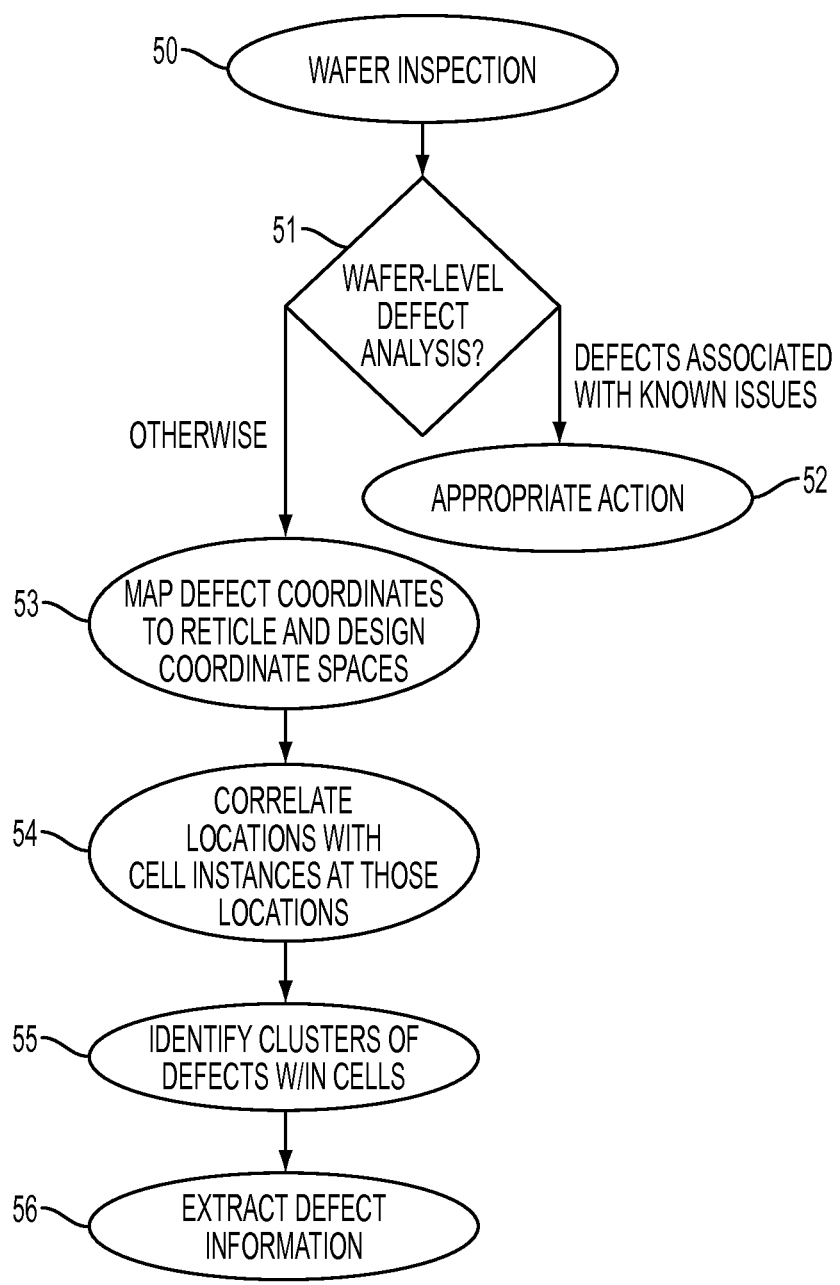
FIG. 2A is an exemplary flow diagram illustrating a method of identifying systematic defects in wafer processing.

With reference to FIG. 2A and, in accordance with an embodiment of the invention, a method for identifying systematic defects is provided and includes wafer based defect analysis, wafer-to-reticle defect stacking, reticle-to-design defect mapping and design-to-cells defect mapping.

In greater detail, the method includes initially performing defect inspection of a plurality of wafers (50). Detected defects are analyzed (51) for trivial and/or known root causes, such as polishing scratches, by way of standard analysis techniques used at the wafer-level, such as wafer regionality, temperature mapping and clustering analysis. Appropriate action is taken (52) for conclusive wafer-level analysis results that reveal defects associated with the trivial and/or known root causes and further analysis is started for the defects that are not associated with the trivial and/or known root causes. The identification of defects as not being associated with the trivial root causes includes determinations that the defects occur at statistically significant rates, determinations that the defects are clustered in certain locations or cell instances and determinations that the defects are caused by certain wafer processing operations, such as circuit layout, as opposed to others.

The further analysis of the defects not associated with the trivial and/or known root causes including mapping defect coordinates to reticle and then to design coordinate spaces (53). Once the physical locations of the defects are translated to the design coordinate space in operation 53, the hierarchical description of the design can be employed to correlate the physical locations where each of the defects occurs with cell instances defined for those physical locations (54). That is, the defects are stacked on the coordinate spaces of the cells for which the design contains instances that interact with the defects locations. The defects stacked at the cell level are then clustered (55) using proximity correlation. Clusters at the cell levels are reported (56) for further analysis.

Figure 2B:
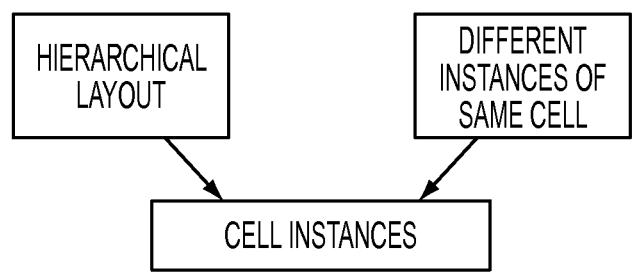
FIGS. 2B and 2C are flow diagrams illustrating derivations of cell instances for FIG. 2A.
Figure 2C:
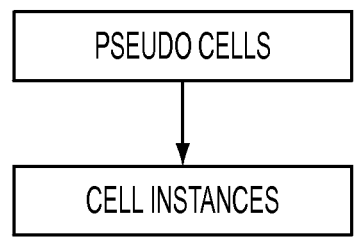

With reference to FIGS. 2B and 2C, cells may be derived directly from the hierarchical layout of the design and/or may be defined using low level shapes or attributes similarity to mimic a hierarchical description, in which case the defined cell is referred to as pseudo-cell. For example, pseudo cells may be defined by equating cells with very similar layouts or by defining a specific back-end-of-line (BEOL) layout, such as, for example, a specific set of structures on various chip layers like a pattern of vias or an end-of-line wire shape. In other cases, pseudo cells may be defined based on image processing or pattern recognition analysis of the layout, they may be different instances of the same cell or they may be qualified by other characteristics of the instance, such as orientation, proximity to the center or edges of the chip or location within the reticle, adjacency to other structures, cells or circuits or they may be defined based on behavior or test results (e.g., by comparing passing cells with failing cells). Thus, as an example, the cell instances may include pseudo-cell instances derived from a hierarchical layout of the design, and cells that define a specific back end of line (BEOL) layout, cells that have similar image processing results and cells that are identified by pattern recognition.

Once the defect mapping (54) is complete, clusters of defects can be identified within certain cells (55) and defect information for identified clusters is extracted (56) for root cause analysis.

The defect mapping (54) can be extended to include secondary design characteristics, such as power, timing, logic organization, test and test coverage, diagnostics, robustness, density, proximity to a change in density, and layout structure sensitivity. These various characteristics may be determined for nets and nodes in the design. The shapes or areas associated with these nets or nodes can be "tagged" with these characteristics. The tags can be used to determine which defects should be combined together. This includes the ability to group defects by net characteristics and by regions of density. For example, the defect mapping may identify defects that occur in certain cell instances with low power, defects that occur in certain cell instances with unclosed timing and defects that occur on nets that carry high currents.

The tags can also be used to determine which groups of defects should be compared to each other. For example, defects that occur in certain cell instances with low power tags can be compared with defects that occur in certain cell instances with high power tags. Similarly, defects that occur in shapes associated with nets with no single vias can be compared with defects that occur in shapes associated with nets with multiple single vias, defects that occur in arrays with one type of array cell can be compared with defects that occur in arrays with another type of array cell, defects in robust versions of a circuit can be compared with defects in un-robust versions of the same circuit and defects from tested areas of a chip can be compared with defect from those not tested.

Figure 4:
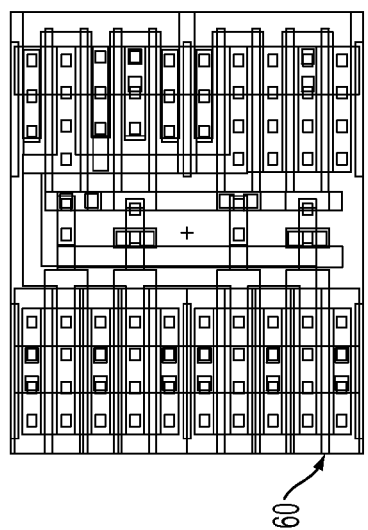
FIG. 4 is a schematic illustration of a cell used in the hierarchical layout of the chip of FIG. 3.
Figure 3:
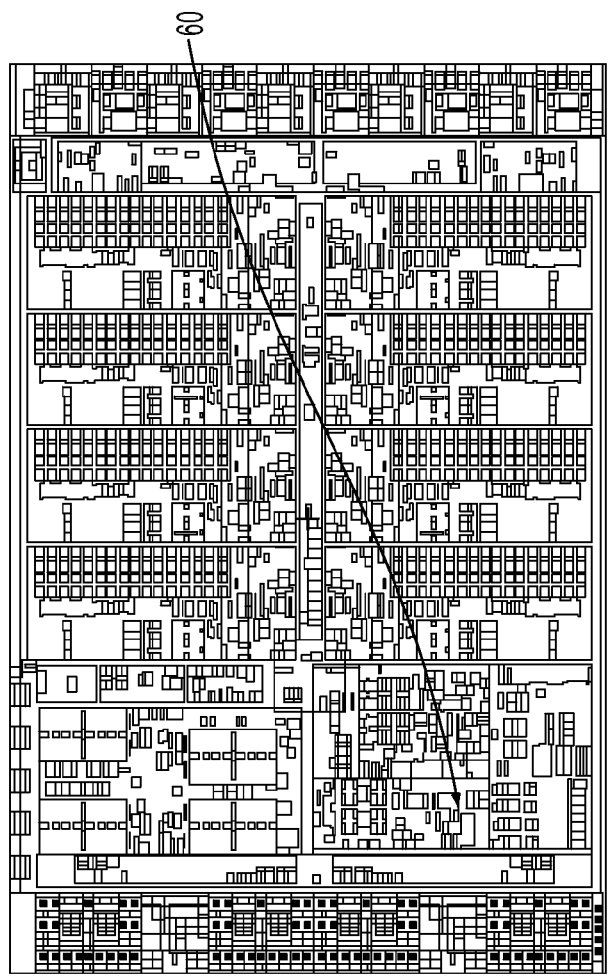
FIG. 3 is an exemplary hierarchical layout design of a chip.
Figure 5:
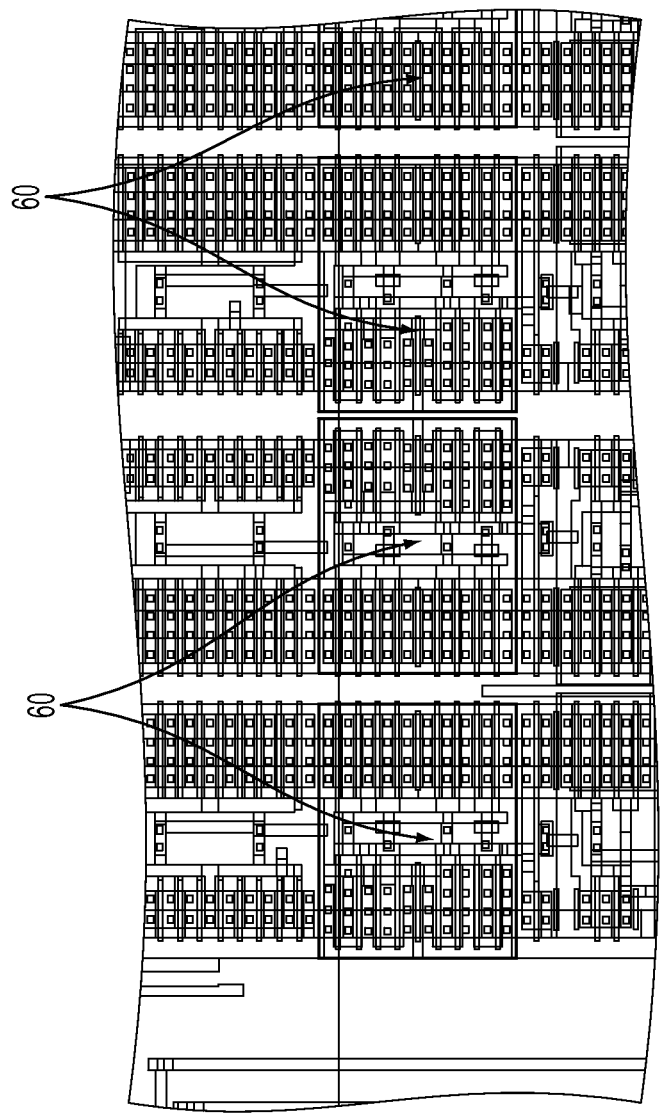
FIG. 5 is an enlarged section of the hierarchical layout of the chip of FIG. 3 in which the cell of FIG. 4 is instantiated multiple times with various orientations.

With reference to FIGS. 3-7, the method illustrated by the exemplary flow diagram of FIG. 2A can be applied. FIG. 3 is an exemplary hierarchical layout of a design in which cell instance 60 is provided in the hierarchical layout and FIG. 4 is an enlarged schematic illustration of the cell instance 60. As shown in FIG. 5, which is an enlarged section of the hierarchical layout of the design of FIG. 3, the cell instance 60 may be provided or built multiple times with multiple orientations and at multiple positions in the hierarchical layout. The various multiple orientations and multiple positions of cell instance 60 would be known ahead of time.

Figure 6:
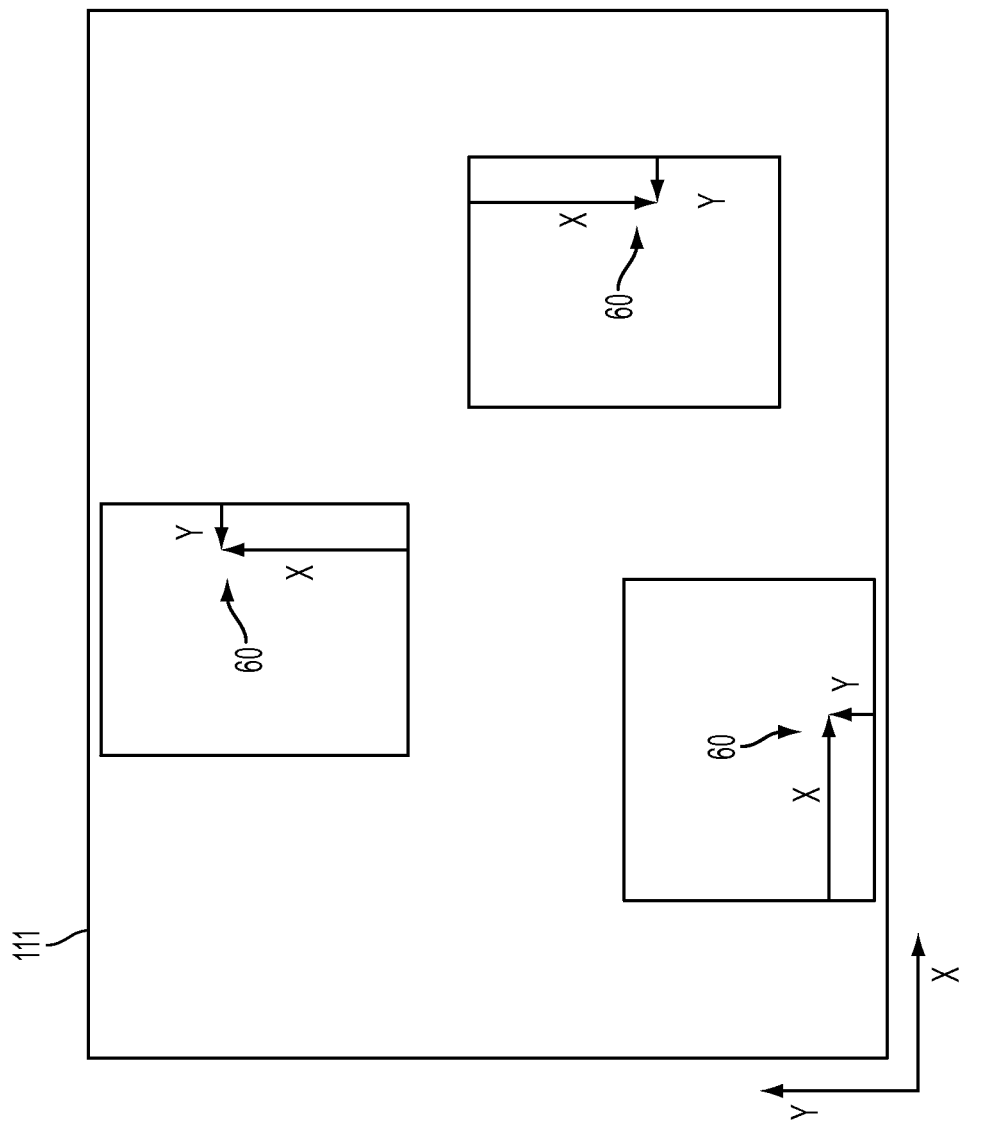
FIG. 6 is a schematic illustration of three cell instances disposed on a chip in various formations highlighting a single cell space location translated to three instance locations in chip coordinate space.
Figure 7:
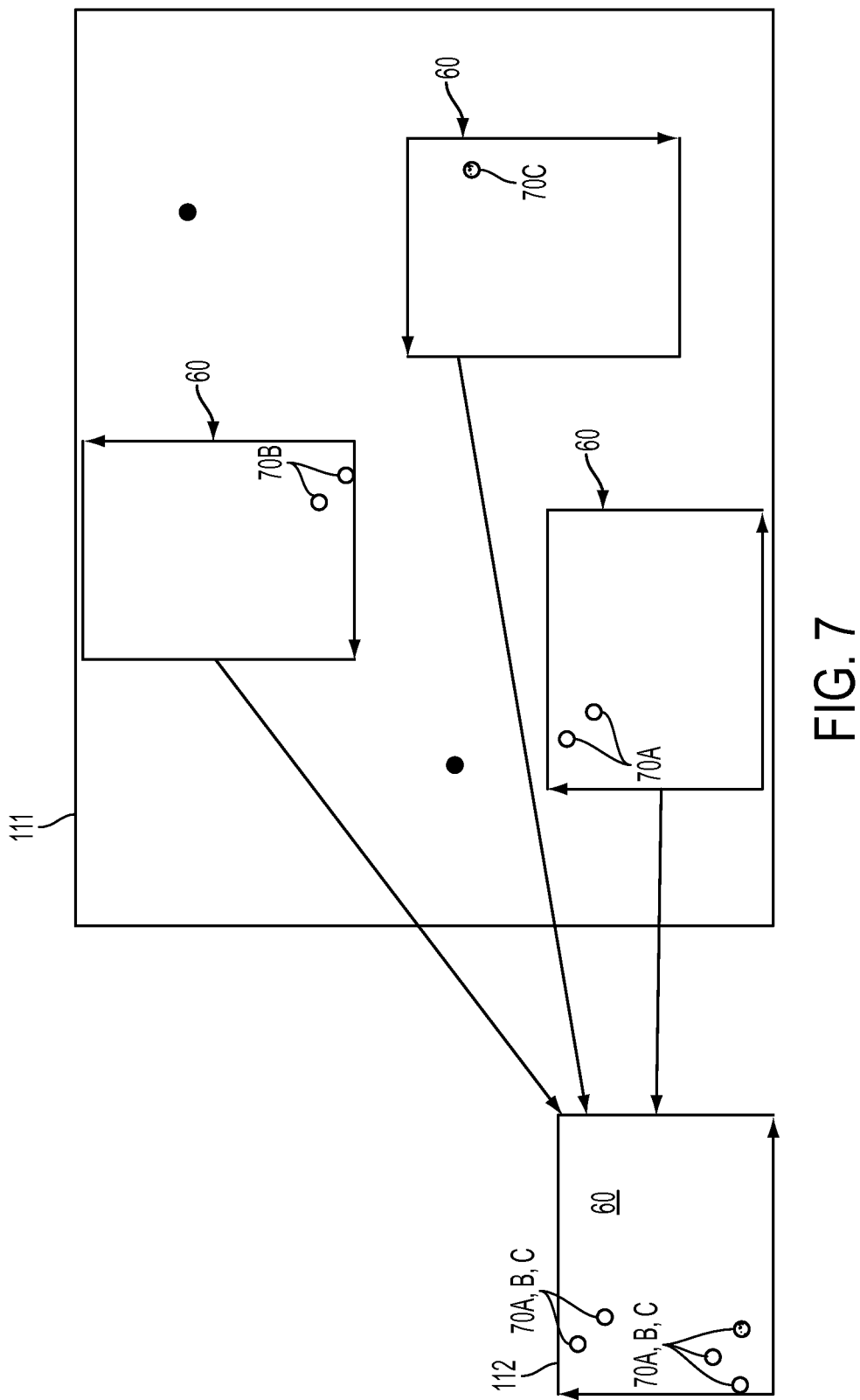
FIG. 7 is a map of identified defects mapped from chip coordinate space to cell space.

Thus, with reference to FIG. 6, which is a schematic illustration of cell instances 60 and/or similar cell instances, it is to be understood that the cell instances 60 may be disposed on a chip 111 multiple times and in various formations. For example, cell instance 60 could be disposed such that an X-Y coordinate axis relative to the cell instance 60 is aligned with an X-Y coordinate axis of the chip 111. By contrast, the X-Y coordinate axis of cell instance 60 could be oriented transversely with respect to the X-Y coordinate axis of the chip 111 or even oriented transversely and negatively with respect to the X-Y coordinate axis. In this way, as shown in FIG. 7, seven defects are identified and overlaid on the X-Y coordinate space of the chip 111. The defects 70A, 70B, and 70C correlate to cell instances 60 and are mapped and stacked on the cell coordinate space 112 for proximity clustering analysis.

This exemplary analysis may hint that the specific locations of the layout of the cell where the defects are clustered is interacting negatively with the manufacturing process and thus is giving rise to defects.

Figure 8:
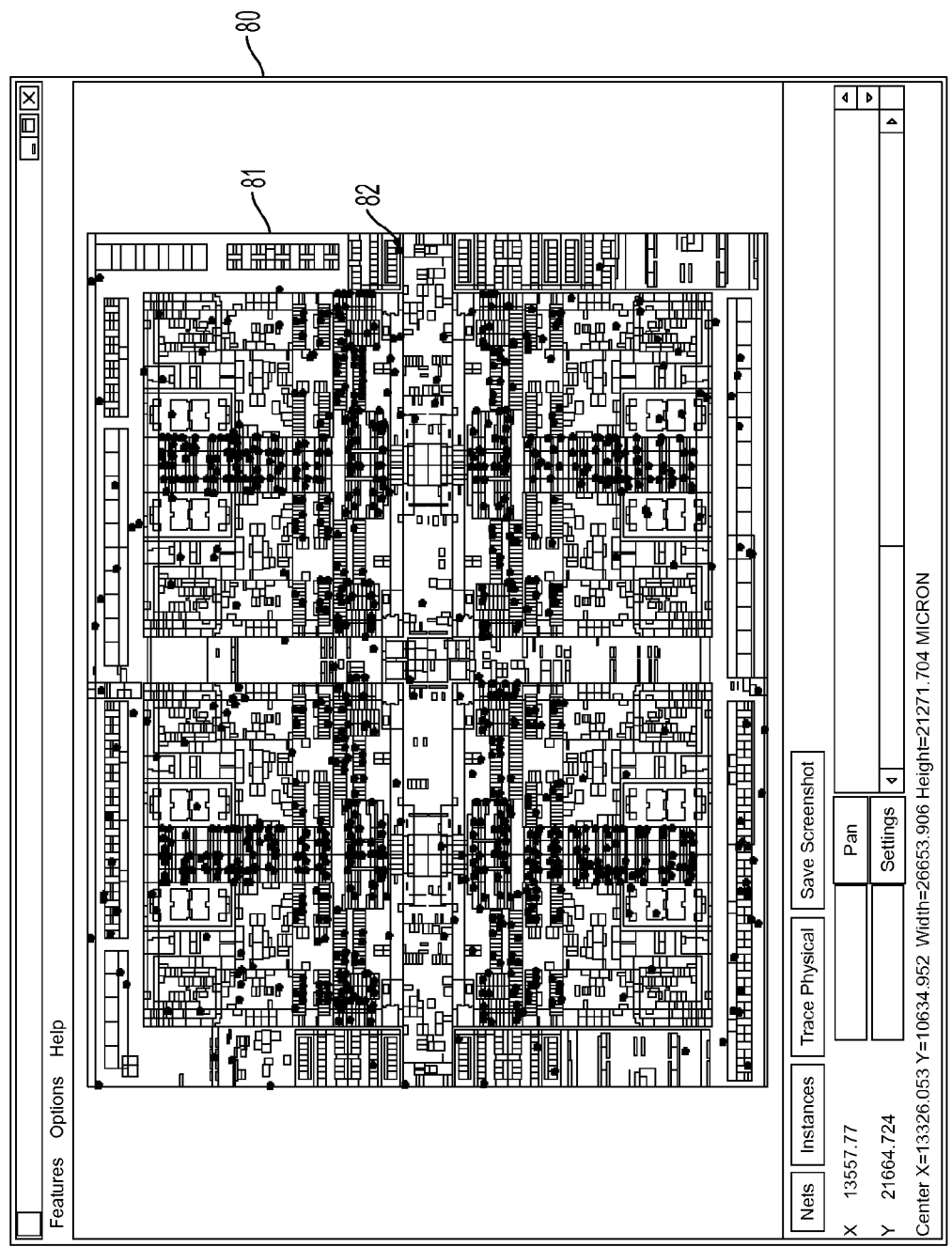
FIG. 8 is an exemplary map of chip level defect clusters.
Figure 9:
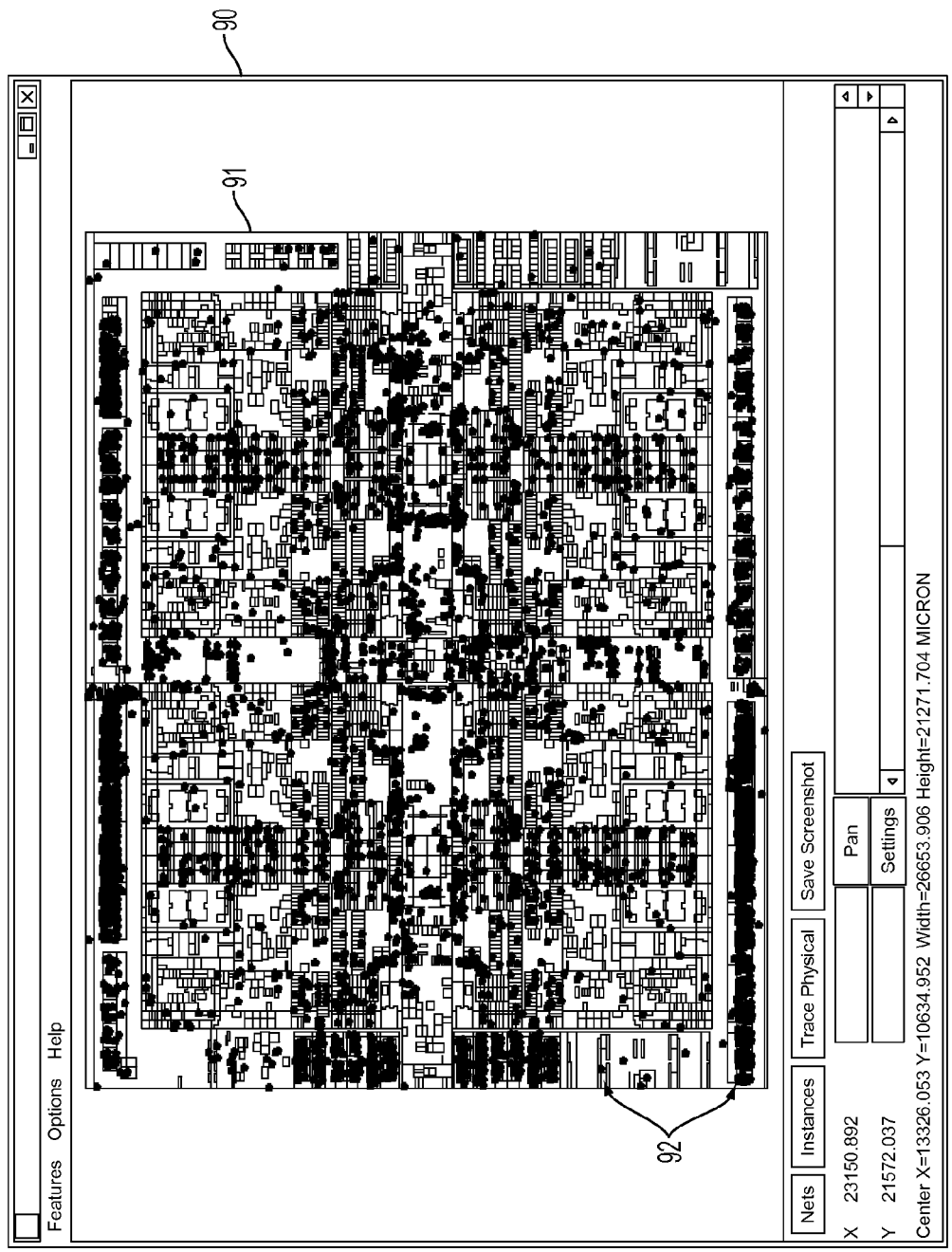
FIG. 9 is an exemplary map of cell level defect clusters.

With reference to FIGS. 8 and 9, it is to be understood that the methods described above may identify a greater number of defects as being systematic due to the fact that seemingly unrelated defects at the chip level may map to nearby locations in some cell coordinate space. This is shown schematically in FIGS. 8 and 9, which each illustrate systematic defects identified as being worthy of consideration by the study of chip or wafer level defect clustering, as in FIG. 8, and by the study of cell level defect clustering of embodiments of the present invention, as in FIG. 9.

As shown in FIG. 8, a display unit 80 provides a readout 81 illustrating systematic defects identified by the study of chip or wafer level defect clustering as being worthy of consideration as black dots 82. By contrast, as shown in FIG. 9, a display unit 90 provides a readout 91 illustrating systematic defects identified by the study of cell level defect clustering of embodiments of the present invention as worthy of consideration as black dots 92 in far greater numbers than those of FIG. 8. This suggests that the numbers of defects identified by the study of cell level defect clustering of embodiments of the present invention has a greater tendency to identify systematic defects than prior methods.

While the disclosure has been described with reference to exemplary embodiments, it will be understood by those skilled in the art that various changes may be made and equivalents may be substituted for elements thereof without departing from the scope of the disclosure. For instance, wafers may contain multiple designs to accommodate manufacturing multiple products within the same wafer. As such, the present invention can be applied on wafers containing a plurality of designs. Also, defects may interact with instances of multiple cells, in which case the defects can be mapped to multiple cell coordinate spaces, and can be clustered multiple times. In addition, many modifications may be made to adapt a particular situation or material to the teachings of the disclosure without departing from the essential scope thereof. Therefore, it is intended that the disclosure not be limited to the particular exemplary embodiment disclosed as the best mode contemplated for carrying out this disclosure, but that the disclosure will include all embodiments falling within the scope of the appended claims.

What is claimed is:

1. A method for identifying systematic defects in wafer processing, comprising:
    performing defect inspection of a plurality of wafers;
    identifying defects in each of the plurality of wafers as not being associated with a trivial and/or known root cause;
    determining a physical location on each wafer where each of the defects occurs; and
    correlating the physical locations where each of the defects occurs with each one of different cell instances of a same cell respectively defined for those physical locations, the different cell instances having multiple rotational orientations in a hierarchical layout,
    the correlating comprising:
        normalizing the respective rotational orientations of the different cell instances into a single rotational orientation relative to layout geometry; and
        defect mapping to the different cell instances based on the single rotational orientation relative to the layout geometry,
    wherein the method is performed using a computer or a processor.

2. The method according to claim 1, wherein the performing of defect inspection comprises wafer based defect inspection.

3. The method according to claim 2, further comprising discarding the defects associated with trivial and/or known root causes.

4. The method according to claim 1, wherein the identifying of defects as not being associated with a trivial and/or known root cause comprises determining that the defects occur at a statistically significant rate.

5. The method according to claim 1, wherein the identifying of defects as not being associated with a trivial and/or known root cause comprises determining that the defects are clustered.

6. The method according to claim 1, wherein the identifying of defects as not being associated with a trivial and/or known root cause comprises determining a cause of the defects.

7. The method according to claim 1, wherein the determining of the physical locations comprises defect mapping.

8. The method according to claim 1, wherein the defect mapping is based on secondary design considerations.

9. The method according to claim 8, wherein the secondary considerations comprise power, timing, logic organization, test and test coverage, diagnostic, robustness, pattern density, proximity to a change in pattern density, and sensitive layout structures.

10. The method according to claim 1, wherein the cell instances are derived from a hierarchical layout of multiple designs of each of the plurality of wafers.

11. The method according to claim 1, wherein the cell instances comprise pseudo-cell instances derived from a hierarchical layout of each of the plurality of wafers.

12. The method according to claim 11, wherein pseudo cells comprise similar cell layouts, cells that define a specific back end of line (BEOL) layout, cells that have similar image processing results and cells that are identified by pattern recognition.

13. A non-transitory computer readable medium on which executable instructions are stored, which, when executed, cause a processing unit of a computing device to perform the method according to claim 1.

14. A method for identifying systematic defects in wafer processing, comprising:
    inputting defect data for a plurality of wafers into a processing unit of a computing device having a non-transitory computer readable medium on which executable instructions are stored, which, when executed, cause the processing unit to:
    analyze wafer level defect data to identify defects with trivial and/or known root causes,
    ascertain defect coordinates,
    translate defects coordinates to reticle and design coordinate spaces, and
    extract placement information for each one of different cell instances of a same cell of each reticle and design coordinate space, the different cell instances having multiple rotational orientations;

normalize the respective rotational orientations of the different cell instances into a single rotational orientation; and defect map the defects to the different cell instances of the reticle and design coordinate spaces based on the single rotational orientation.

15. The method according to claim 14, wherein the executable instructions, when executed, further cause the processing unit to compare the wafer level defect data against design rule checking results.

16. The method according to claim 14, wherein the executable instructions, when executed, further cause the processing unit to:

identify clusters of defects within each cell of each design based on correlation between the defect coordinates and the design coordinates, and extract defect information associated with the wafer level defect data clustered within each cell of each design.

17. A method for identifying systematic defects in wafer processing comprising wafer based defect analysis, wafer-to-reticle defect stacking, reticle-to-design defect mapping and design-to-cells defect mapping, the design-to-cells defect mapping comprising:

normalizing into a single rotational orientation respective rotational orientations of different cell instances of a same cell where occurrences of defects not associated with trivial and/or known root causes are located; and defect mapping the defects to the different cell instances based on the single rotational orientation, wherein the method is performed using a computer or a processor.

18. A system to identify systematic defects in wafer processing, comprising:

a wafer inspection apparatus to inspect a plurality of wafers for defects and to generate defect data in accordance with results of the inspection;

a networking unit coupled to the wafer inspection apparatus; and a computing device, coupled to the networking unit, to receive the defect data generated by the wafer inspection apparatus by way of the networking unit, the computing device including a processing unit and a non-transitory computer readable medium on which executable instructions are stored, which, when executed, cause the processing unit to identify defects in each of the plurality of wafers as not being associated with trivial and/or known root causes, to determine a physical location on each wafer where each of the defects occurs and to correlate the physical locations where each of the defects occurs with each one of different cell instances of a same cell respectively defined for those physical locations, the different cell instances having multiple rotational orientations, the correlation being executed by:

a normalization of the respective rotational orientations of the different cell instances into a single rotational orientation; and a defect mapping to the different cell instances based on the single rotational orientation.

* * * * *